Figure 1:
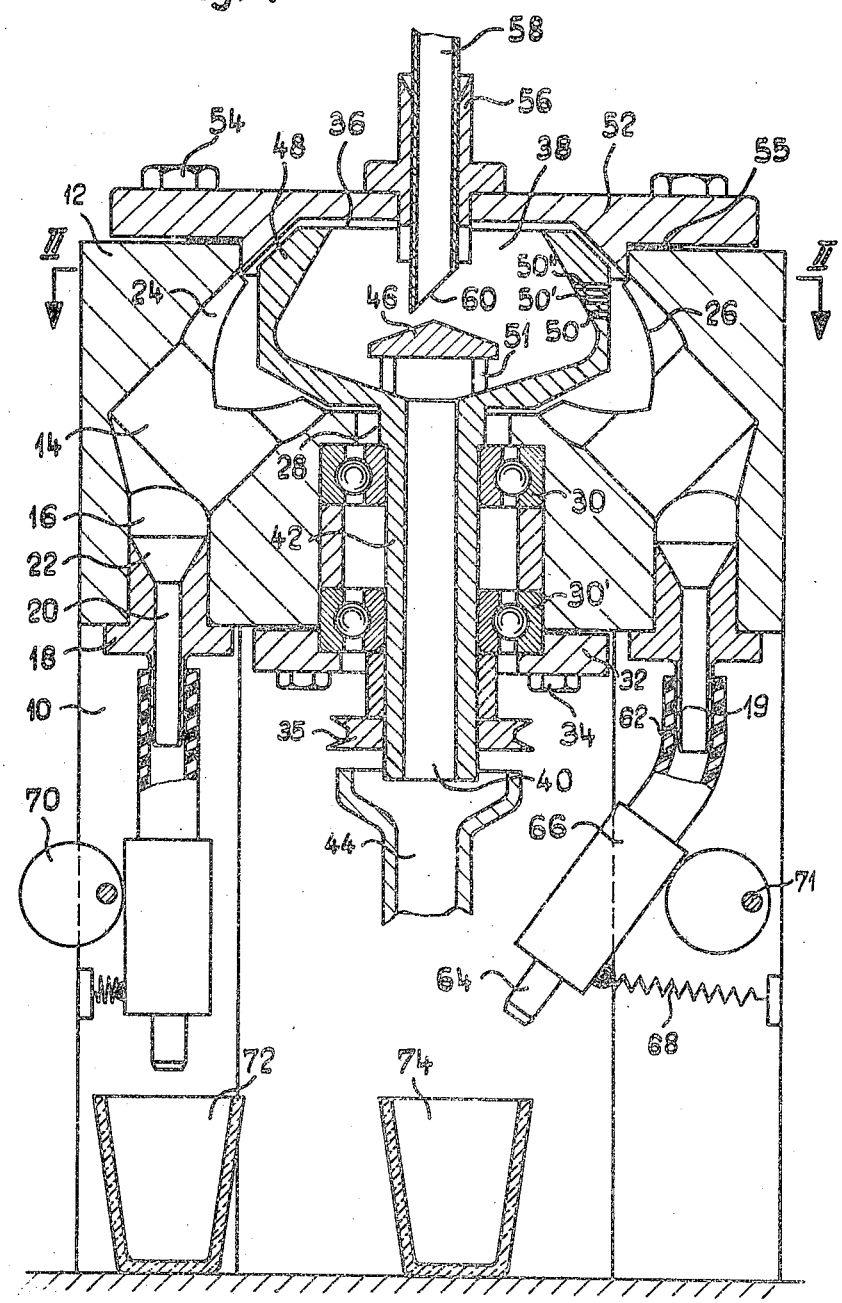

United States Patent [19]

Schurmann

[11] 4,126,043

[45] Nov. 21, 1978

[54] APPARATUS FOR DIVIDING A LIQUID INTO PRECISELY DEFINED ALIQUOTS

[75] Inventor: Werner Schürmann, Greifensee, Switzerland

[73] Assignee: Mettler Instrumente AG, Greifensee-Zurich, Switzerland

[21] Appl. No.: 831,248

[22] Filed: Sep. 7, 1977

[30] Foreign Application Priority Data

Nov. 30, 1976 [CH] Switzerland ............... 15021/76

[51] Int. Cl.² .................................................. G01N 1/18
[52] U.S. Cl. ............................................. 73/424; 141/34
[58] Field of Search ................... 73/424; 222/410; 141/34, 102

[56] References Cited

U.S. PATENT DOCUMENTS

| 1,208,373 | 12/1916 | Rhodes | 73/424 |
| 2,837,920 | 6/1958 | Keith | 73/424 |
| 3,098,390 | 7/1963 | Bourne et al. | 73/424 |
| 3,590,642 | 7/1971 | Root | 73/424 |
| 3,747,622 | 2/1973 | Reinhall | 73/424 X |

Primary Examiner—Charles Gorenstein

[57] ABSTRACT

An amount of liquid is divided into precisely defined aliquots by discharging the liquid by centrifugal force from a single radial opening in a spinning bowl against a circular row of knife-edged partitions defining receptacles therebetween.

12 Claims, 2 Drawing Figures

APPARATUS FOR DIVIDING A LIQUID INTO PRECISELY DEFINED ALIQUOTS

BACKGROUND OF THE INVENTION

This invention relates to the dividing of an amount of liquid into several portions in a precise, predetermined ratio, and particularly to apparatus for so dividing liquid.

During chemical analysis, it is often necessary to separate a precisely defined portion of a body of liquid from the remainder of the body. A pipette is the instrument conventionally employed for manually withdrawing an aliquot from a body of liquid to be analyzed, and automatic pipettes have been used in automatic apparatus for chemical analysis in which several aliquots often have to be drawn from the same body of liquid. Automatic pipettes satisfying requirements for high precision are relatively complex, and they are costly to build and to maintain in good working condition.

It is a primary object of this invention to provide apparatus capable of dividing an amount of liquid into a plurality of portions in a precise, predetermined ratio which apparatus is simpler than an automatic pipette and less costly to build and operate.

With this object and others in view, as will hereinafter become apparent, the invention provides a normally stationary support on which a bowl is mounted for movement about an axis of rotation. An axially extending wall bounds a cavity in the bowl capable of containing the liquid to be divided during rotation of the bowl. The wall is formed with a passage extending therethrough between a first orifice communicating with the bowl cavity and a second orifice spaced radially outward from the first orifice relative to the axis of rotation. When the bowl is rotated about its axis at adequate speed, the second orifice moves in a radial plane and discharges liquid by centrifugal force.

Several partition walls mounted on the support and transversely intersecting the afore-mentioned radial plane define therebetween receptacles on the support which are open toward the liquid-discharging orifice and each receive a portion of the discharged liquid. The several portions may be withdrawn separately from the several receptacles through suitable draining devices.

Figure 2:
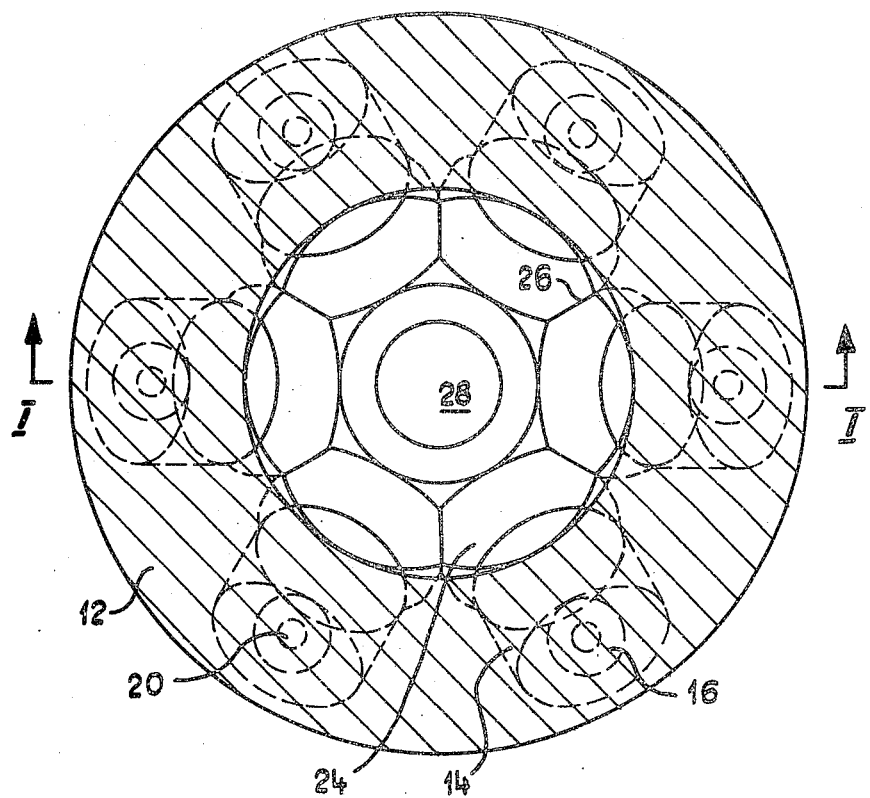

Other features, additional objects, and many of the attendant advantages of this invention will readily be appreciated as the same becomes better understood by reference to the following detailed description of a preferred embodiment when considered in connection with the appended drawing in which:

FIG. 1 shows apparatus of the invention in elevational section on the line I—I in FIG. 2; and FIG. 2 illustrates a portion of the apparatus of FIG. 1 in plan section on the line II—II.

Referring now to the drawing in detail, and initially to FIG. 1, there is seen liquid dividing apparatus of the invention which has many features in common with a conventional, continuously operating centrifugal separator.

It includes a sturdy supporting frame 10 on which a unitary, metallic stator 12 is fixedly mounted. The stator 12 is of generally cylindrical shape about an upright axis and is shown separately in FIG. 2. Six identical chambers 14 in the stator are each of at least partly circular cross section about respective axes of curvature which are located in a common conical surface about the stator axis, that is, the several axes of curvature intersect the stator axis at the same point at identical angles of 45° and diverge downward from the point of intersection in equiangular distribution about the stator axis.

Axial bores 16 in the stator 12 provide separate draining outlets from the lowermost portions of the several chambers 14 and receive respective flanged, tubular plugs 18 from which nipples 19 project downwardly. The ducts 20 in the plugs 18 and nipples 19 have conically flaring upper orifices. The upper ends 24 of the chambers 14 are similarly enlarged so that the partition wall separating each chamber 14 from adjacent chambers ends in an almost vertical knife edge 26.

The stator 12 has a central bore 28 which varies in diameter along its axial length. Its very wide top portion communicates with the upper ends 24 of the chambers 14. Two ball bearings 30, 30' are coaxially retained in the bore 28 in axially spaced relationship by a flat retaining ring 32 attached to the bottom face of the stator 12 by screws 34. A tubular drive shaft 42 journaled in the bearings 30, 30' carries a pulley 35 at its lower end outside the bore 28 and an integrally attached bowl 36 at its upper end in the wide top portion of the bore 28.

The cavity 38 of the bowl 36 has a major portion conically tapering in an upward direction at an acute angle of about 60° to the wide open top of the bowl, while a minor bowl portion tapers conically downward from the base of the major portion at an obtuse angle to an orifice of the bore 40 in the drive shaft 42. A stationary waste line 44 is mounted on the frame 10 below the lower orifice of the drive shaft 42 in a manner not specifically shown. The upper orifice of the bore 40 is spacedly covered in the cavity 38 by a conical baffle 46 removably mounted on upright legs 51. Three radial bores 50, 50', 50" are provided in the axially extending wall 48 of the bowl 36 in respective radial planes perpendicular to the axis of rotation of the drive shaft 42 and of the bowl 36 slightly above the baffle 46 and intersecting the knife edges 26. The radially inner orifices of the bores 50, 50', 50" communicate directly with the major portion of the cavity 38, and their outer orifices are located one above the other in the outer surface of the wall 48.

The stator bore 28 is upwardly closed by a cover 52 fastened to the top surface of the stator 12 by screws 54. An annular gasket 55 prevents liquid from leaking between the cover 52 and stator 12. A flanged sleeve 56 centrally set into the cover 52 receives a supply pipe 58 whose lower end axially extends into the bowl cavity 38 and has an oblique, annular end face 60.

Only two of the six plugs 18 and nipples 19 are shown in FIG. 1 in order not to crowd the drawing. A flexible hose 62 of reinforced elastomeric material is slipped over each nipple 19 and leads into a heavy-walled, rigid tube 66 from which a discharge spout 64 depends. A helical tension spring 68 attached to the frame 10 holds each tube 66 in contact with the cylindrical face of a disc 70 eccentrically mounted on a shaft 71. The shaft is received in a bore of the frame 10 with sufficient friction that the spring 68 cannot turn the disc 70 from its angular position. In the illustrated position of the discs 70, one of the spouts 64 is directed straight down from the associated nipple 19 toward the open top of a beaker 72, while the other spout 64 is directed toward a beaker 74 stationed below the center of the stator 12.

The illustrated apparatus may be operated as follows:

The rotor assembly consisting of the bowl 36 and the drive shaft 42 is rotated at high speed (3000–9000 RPM) by a belt trained over the pulley 35 and a corresponding larger pulley on the output shaft of an electric motor in a conventional manner, not shown. The liquid to be divided into aliquots is fed to the cavity 38 of the rotating bowl 36 through the supply pipe 58. The entering liquid is deflected by the baffle 46 toward the rapidly rotating wall 48 and rises along the wall to the inner orifice of the bore 50. The liquid is discharged by centrifugal forces in a single radial jet intersecting the several knife edges 26 and thereby divided precisely between the several receptacles of the stator 12 in the chambers 14 and associated openings separated by integral partition walls of the stator. Each receptacle tapers gradually from the upper end 24 of the corresponding chamber 14 to the nipple 19 and practically no liquid is retained in the descending flow path to the spout 64. If liquid is trapped in the widest part of the bowl 36, it can be dislodged by a washing liquid which also is uniformly distributed among the several receptacles.

If a solid precipitate was initially suspended in the supplied liquid, it collects in the bowl 36, and remains there even after washing in the rotating bowl. It may be flushed from the arrested bowl through the bore 40 into the waste line 44. If no solid matter needs to be separated from the divided liquid, the baffle 46 may be replaced by a plug entering the bore 40 and having an enlarged head in the cavity 38 as not specifically illustrated.

The receptacles of an actual embodiment of the illustrated stator 12 divide the supplied liquid into six portions which differ from each other by not more than one part in one thousand. The partitions terminating in the knife edges 26 are machined with the necessary precision out of a solid block of metal in a relatively simple manner, the machining operation being further facilitated by the conical distribution of the receptacle axes.

The discharged liquid portions may be collected separately or combined again in any desired manner by manipulating the discs 70. Thus, six equal aliquots may be collected in individual beakers as is shown at 72, or as many as five aliquots may be collected in a centrally stationed, common vessel in the manner shown at 74. Ultimately, the apparatus may be used as a centrifugal separator and all the supernatant combined in one container toward which each of the six spouts 64 is aimed by the associated discs 70.

The rate of liquid supply to the bowl cavity 38 is preferably controlled in such a manner that the liquid passes through the bowl wall 48 only in the bore 50. There is a slight loss in precision if the liquid is supplied fast enough to cause intermittent discharge from one or both of the safety passages provided by the bores 50', 50". The three bores have been shown in FIG. 2 to be located in a common plane through the axis of rotation, and it is convenient for a machinist to arrange them in this manner. Their circumferential distribution in the wall 48, however, is irrelevant to their function.

The number of knife edges 24 will be chosen to suit specific requirements, and laboratory size apparatus of the invention having four to twelve knife edges has been operated successfully. If equal portions of a body of liquid are to be separated from each other, the knife edges intersect the radial plane defined by the outer orifice of the bore 50 at equiangularly distributed points, as specifically illustrated, but other distributions of the knife edges may be chosen to suit specific tasks.

While manual adjustment of the discs 70 was implied above, the apparatus of the invention is well suited as a component in a fully automatic analysis arrangement in which the discs may be turned by automatic controls in any desired sequence.

The illustrated supply pipe 58 precisely directs the liquid fed to the bowl toward the baffle 46 for even distribution over the inner face of the wall 48 so that liquid may be processed by a small bowl 36 at a high rate. The amount of liquid retained in the pipe by surface tension is reduced to a minimum by the pointed lower end defined by the oblique end face 60.

It should be understood, of course, that the foregoing disclosure relates only to a preferred embodiment of the invention, and that it is intended to cover all changes and modifications of the example of the invention herein chosen for the purpose of the disclosure which do not constitute departures from the spirit and scope of the appended claims.

What is claimed is:

1. Apparatus for dividing an amount of liquid into a plurality of portions in a precise, predetermined ratio comprising:
   (a) a normally stationery support;
   (b) a bowl mounted on said support for movement about an axis of rotation;
     (1) said bowl including an axially extending wall bounding a cavity in said bowl capable of containing said liquid during said movement,
     (2) said wall being formed with a passage extending therethrough between a first orifice communicating with said cavity and a second orifice spaced radially outward from said first orifice relative to said axis,
     (3) said second orifice moving in a plane radial relative to said axis during said movement of said bowl for centrifugal discharge of said liquid in said plane;
     (4) and drive means for rotating said bowl about said axis at a speed sufficient for causing said centrifugal discharge;
   (c) a plurality of partition walls mounted on said support and transversely intersecting said plane,
     (1) said partition walls being spaced from each other circumferentially relative to said axis,
     (2) each pair of circumferentially adjacent partition walls defining therebetween a receptacle on said support open toward said second orifice for receiving a portion of the centrifugally discharged liquid; and
   (d) draining means for separately withdrawing the portions of said liquid received in at least two of said receptacles.

2. Apparatus as set forth in claim 1, wherein said orifice moves in a circle during said movement of said bowl, and said partition walls are spaced from said circle in a radially outward direction.

3. Apparatus as set forth in claim 2, wherein said partition walls each have a sharply angular edge portion transversely intersecting said plane and facing said second orifice during said rotation.

4. Apparatus as set foth in claim 2, further comprising supply means for supplying said liquid to said cavity during said rotation.

5. Apparatus as set forth in claim 4, wherein said supply means include an elongated tubular member formed with a longitudinal bore and having an end face in said cavity obliquely inclined relative to the direction of elongation thereof and to said bore.

6. Apparatus as set forth in claim 2, wherein said partition walls intersect respective portions of said plane equiangularly distributed about said axis.

7. Apparatus as set forth in claim 6, wherein said recystacles are substantially identical.

8. Apparatus as set forth in claim 7, wherein each of said receptacles has a portion of circular cross section about an axis of curvature obliquely intersecting said axis of rotation at substantially the same angle in substantially the same point.

9. Apparatus as set forth in claim 8, wherein said receptacles each include outlet means for discharge of the received liquid portion by gravity, and said draining means include a flexible elongated tube having one longitudinally terminal portion attached to and communicating with one of said outlet means, and shifting means for flexing said tube and thereby shifting the other longitudinally terminal portion of said tube.

10. Apparatus as set forth in claim 1, further comprising outlet means on said bowl for discharge of liquid from said cavity by gravity, and a baffle in said cavity for deflecting liquid from said outlet means during said movement of said bowl.

11. Apparatus as set forth in claim 1, wherein said axially extending wall is formed with an additional passage extending therethrough, said additional passage having an inner orifice communicating with said cavity and an outer orifice spaced radially outward from said inner orifice, said first orifice and said inner orifice being spaced in the direction of said axis of rotation.

12. Apparatus as set forth in claim 10, wherein said second orifice is the only orifice in the outer surface of said axially extending wall in said radial plane.

* * * * *